United States Patent [19]

Helmy

[11] Patent Number: 5,437,605

[45] Date of Patent: Aug. 1, 1995

[54] REMOTE CONTROLLABLE PENILE PROSTHETIC SYSTEM

[76] Inventor: Ali M. Helmy, Bokami Building, Palestine Street, Makarona Cross Flat 304, Jeddah 21414, Saudi Arabia

[21] Appl. No.: 67,950

[22] Filed: May 27, 1993

[51] Int. Cl.[6] ............................................... A61F 2/26
[52] U.S. Cl. ...................................................... 600/40
[58] Field of Search .................................... 600/40–41

[56] References Cited

U.S. PATENT DOCUMENTS

| | | | |
|---|---|---|---|
| 4,364,379 | 12/1982 | Finney | 600/40 |
| 4,407,278 | 10/1983 | Burton et al. | 600/40 |
| 4,941,461 | 7/1990 | Fischell | 600/40 |

*Primary Examiner*—Lee S. Cohen
*Assistant Examiner*—J. P. Lacyk
*Attorney, Agent, or Firm*—Vorys, Sater, Seymour & Pease

[57] ABSTRACT

An implantable penile prosthesis system which includes a fully implantable and elongatable prosthesis that is operated by remote control.

22 Claims, 8 Drawing Sheets

REMOTE CONTROLLABLE PENILE PROSTHETIC SYSTEM

BACKGROUND OF THE INVENTION

The present invention relates generally to penile erection systems for overcoming erectile dysfunctions. More particularly, it relates to penile erection systems which are remotely controlled and elongatable, as well as a method of operating the same.

A wide variety of approaches have been proposed for overcoming erectile dysfunctions to thereby alleviate the trauma associated therewith. One practice generally accepted is to apply a vasodilator type drug directly to the penis for selectively effecting erections. Significant difficulties tend to arise, however, with the application of these drugs since dosages are usually self-administered by injection. Such injections have a tendency to be both frightening and painful to some patients. In addition, repeated injections may result in hematoma, infection, and eventually penile fibrosis. Consequently, there are significant drawbacks.

Another common approach for overcoming dysfunctions includes utilization of implantable prostheses. A number of different types of prostheses have been proposed. Penile erections are achieved upon selective introduction of fluid to an extensible chamber of the prosthesis implant that is located within a portion of a penis. Essentially, the fluid is transferred from a suitable reservoir, which is either integral with the implant or separate therefrom, through a valve system and finally into an extendable distal end chamber of the prothesis which expands and causes penile erection. Return of the penis to a flaccid condition occurs when the fluid is withdrawn from this distal end chamber and returns to the reservoir.

A variety of mechanisms exist for operating implant systems. The overwhelming majority of them tend to require distinct manual manipulations of a separate reservoir in the form of a bulb or some other comparable component for forcing the fluid into the distendable chamber for effecting an erection. Subsequently, compression of the filled chamber manually effects fluid return to the reservoir to thereby bring about a flaccid penile condition. There are, however, disadvantages associated with such mechanisms, not the least of which includes significant inconvenience, such as in obtaining manual proficiency required in manually pumping the fluid to effect either erect or flaccid penile conditions.

Still another known approach is described in U.S. Pat. No. 4,941,461 issued to Fischell. This patent describes use of a remote control device for remotely controlling erection of a penile prosthetic implant by generating a rapidly alternating magnetic field for inducing operation of a solenoid type pump, which pump is self-contained in the prothesis. In fact, the pump acts to selectively pump fluid for effecting both the erect and flaccid conditions. However, this remote controlled type of prosthesis has several significant drawbacks associated with its use including a shortcoming that a relatively complicated solenoid pump is used which in operation makes a distracting and potentially annoying humming noise.

Accordingly, there exists a continuing desire for improving upon known penile implant systems by providing not only simple, reliable, safe, and easy to operate systems, but ones which can be expeditiously controlled remotely, as well as elongate and contract reliably and automatically.

SUMMARY OF THE INVENTION

In accordance with the present invention there is provided an improved unitary penile prosthetic system which is fully implantable and controlled remotely, as well as a method of operating the same.

Included in this system is an implantable penile prosthesis and a remote controlled device. The prosthesis includes a first fluid chamber assembly operable in response to the flow of pressurizing fluid housed within the prothesis to cause erection and elongation of the penis, as well as, operable in response to forced evacuation of fluid therefrom to effect a flaccid penile condition. A second fluid chamber assembly is provided which is operable for selectively storing fluid from the first chamber assembly when the penis is in the flaccid state and for allowing fluid flow to the first chamber assembly for effecting erection. Included in the prothesis is a fluid transfer assembly that is coupled to and between, as well as cooperates with the first and second chamber assemblies for selectively transferring the fluid therebetween in response to remote control operation. In this regard, the fluid transferring assembly includes an energizable assembly and a valve assembly adapted to cooperate with the energizable assembly for selectively transferring fluid between the first and second chamber assemblies. The energizable assembly includes an electromagnetic unit which when energized displaces a plunger assembly in either one of two opposite directions. Such displacement serves to effect fluid transfer either into or out of the first and second chamber assemblies simultaneously so as to thereby effect erect or flaccid states in the penis depending on the direction of movement of the fluid. In the illustrated embodiment, a remote control device is provided which is operable for selectively controlling the energizable assembly to operate in the described manner.

In another illustrated embodiment, the first chamber assembly is defined by a longitudinally distensible assembly which includes an elongatable bellows and which assembly is in fluid communication with the fluid transfer assembly. The bellows elongates upon introduction of pressurized fluid within the first chamber assembly to thereby effect an erection and elongation of the penis. Withdrawal of the fluid from the first chamber results in the bellows and thereby the penis returning to a flaccid and relatively contracted condition.

In a further illustrated embodiment, the second chamber assembly is formed at a proximal end portion of the prosthesis. The chamber includes an expansible bladder having a reservoir for selectively storing the fluid and a cage which not only facilitates unimpeded expansion and contraction of this chamber, but serves to secure it in the corpus at the penis base. In this regard, the cage prevents suction pressure, created on the surrounding tissue as a result of evacuation of the reservoir bladder, from impeding bladder movement.

In another illustrated embodiment, the electromagnetic means is operable for creating electromagnetic fields which are effective for alternately attracting and repelling the plunger assembly. In response to one electromagnetic state, the plunger assembly is movable for cooperating with a valve means located in a fluid transfer housing for permitting fluid in the reservoir or storage chamber to flow through the transfer housing and into the expansible first chamber assembly.

In a still further illustrated embodiment, the electromagnetic means is selectively energizable for creating an electromagnetic field which displaces the plunger assembly so as to thereby move and cause withdrawal of the pressurizing fluid from the first chamber assembly, whereupon the fluid travels through the transfer assembly, and ultimately into the second chamber assembly.

In a further embodiment, the plunger includes a body supporting a one way-check valve therein and a one-way flap valve.

Accordingly, among the objects which are provided by the present invention are the following: an improved unitary penile prosthetic system which includes a penile prothesis of unitary construction and a remote controlled unit; an improved penile prothesis which is fully implantable and elongatable; an improved penile prosthesis which includes valving structure cooperable with a sliding valved plunger for effecting the desired fluid transfer to achieve erect and flaccid conditions; and an improved unitary prothesis which is simple in construction reliable in operation and relatively inexpensive to manufacture.

Other objects and the full scope of the present invention will become apparent upon review of the detailed description to follow when taken in conjunction with the accompanying drawings in which like parts are designated by like reference numerals throughout the several views.

DETAILED DESCRIPTION

Reference is made to FIGS. 1-6 for illustrating one preferred embodiment of a remote controlled penile prosthetic system 10 which includes a completely implantable and unitary penile prosthesis 12, and a hand-held remote control device 14 for actuating the former to effect erect and flaccid penile conditions. The system 10 is basically operated for selectively effecting erect and flaccid conditions of a penis (not shown) by controlling flow of a self-contained fluid housed in the prosthesis 12 between storage and expandable chambers. The fluid can be pressurized air or a suitable saline solution. The degree of pressurization determined by the amount necessary to achieve the desired prosthetic functions.

Figure 1:
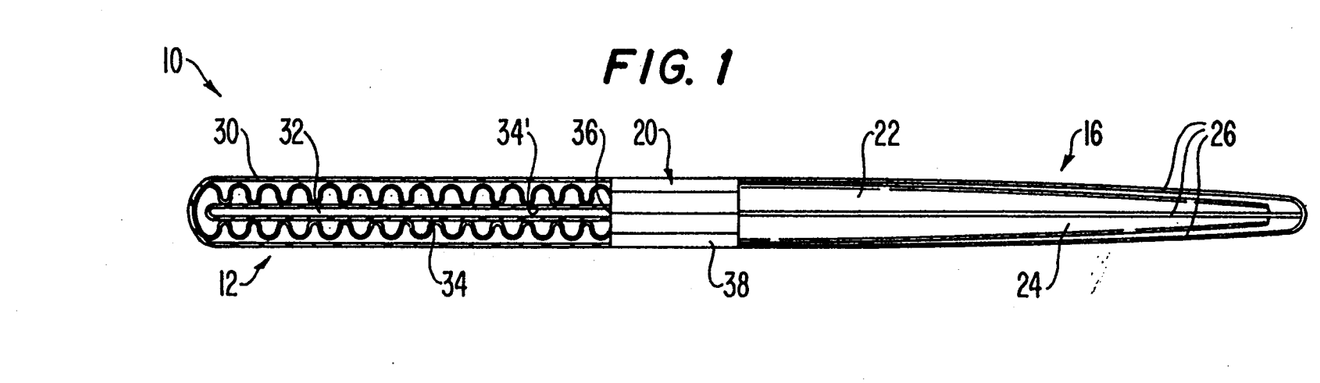
FIG. 1 is a longitudinal view, partly in section, of one preferred embodiment of a penile prosthesis of the present invention.
Figure 2:
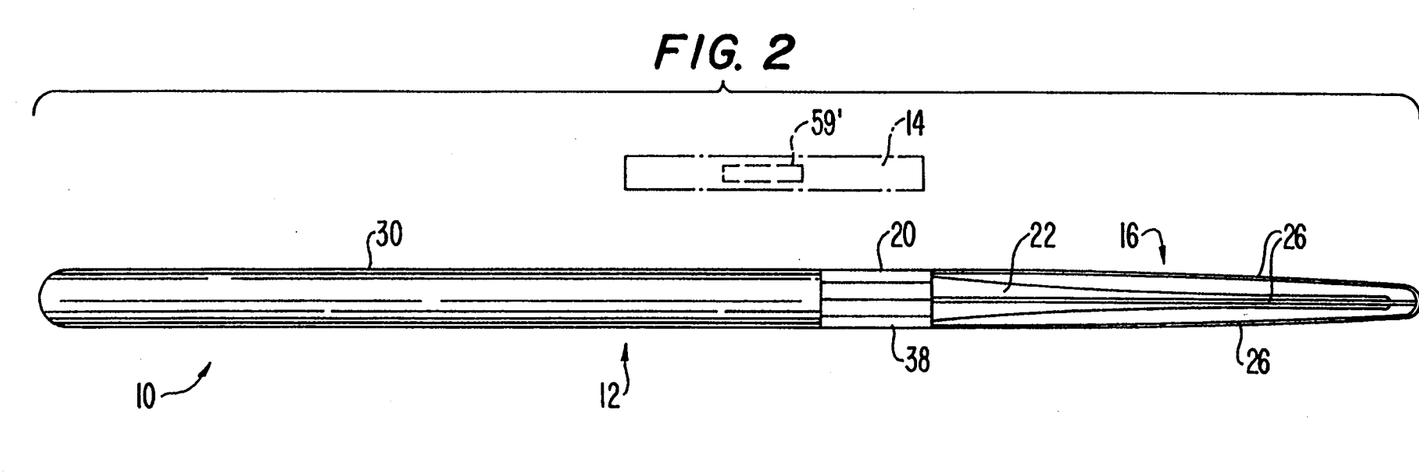
FIG. 2 is a view of the penile prosthesis in an expanded condition.

The longitudinally elongated and implantable prosthesis 12 includes proximal and distal fluid chambers assemblies 16 and 18; respectively, at its opposite ends. Structurally and functionally coupled to and between the proximal and distal chamber assemblies 16 and 18 is a fluid transfer assembly 20. It is the transfer assembly 20 that is operable by the remote control device 14 for effecting displacement of fluid though the assembly 20 and between the chamber assemblies 16 and 18. As will be described, such transfer is effective for causing the noted erect and flaccid penile conditions, as a function of whether the fluid is either entering or exiting the distal chamber assembly 18.

Initial reference is made to the proximal fluid chamber assembly 16. The chamber assembly 16 includes an expandable fluid reservoir 22 which is made of an elongated and expandable bladder of medical grade material, such as silicone rubber. Surrounding this fluid bladder or reservoir 22 is a cage 24 that is also made of a biocompatible material and which is integrally connected at one end thereof to the fluid transfer assembly 20. Specifically, the cage 24 has a generally elongated cylindrical shape that is constructed by a plurality of circumferentially spaced apart and relatively rigid support rods 26 which support the prosthesis 12 in a base of the penis, as well as allows the reservoir 22 to unimpedeling expand and contract when implanted.

Reference is now made to the distal chamber assembly 18 which is illustrated in FIGS. 1 and 2. The distal chamber assembly 18 is adapted to be implanted in a penile corpus cavernosum (not shown). The distal chamber assembly 18 is constructed to expand to thereby effect erection and elongation of the penis upon the pressurized fluid being received therein. Later, the distal chamber assembly 18 collapses upon fluid withdrawal to thereby effect a flaccid penile condition. The distal chamber assembly 18 includes a longitudinal and elongatable outer sheath 30 which is arranged to enclose a collapsible and reciprocatable expandable bellows type reservoir 32 of limited expendability. The outer sheath 30 is also made of a biocompatible plastic material. An anterior bladder 34 defining an anterior chamber 34a is centrally positioned within the bellows 32 and extends along a portion of a longitudinal axis of the chamber assembly 18. The anterior bladder 34 is expandable longitudinally, but does not significantly bulge. The bladder 34 includes a port 36 at one end thereof for allowing fluid transfer between it and the transfer assembly 20. The bellows linearly extends upon longitudinal expansion of the bladder 34, but does not necessarily bulge.

Whenever the distal fluid chamber assembly 18 is void of fluid, it is thus in a non-expanded condition (FIG. 1) and the penis will be in a flaccid condition (not shown). FIG. 2 on the other hand represents the expanded and elongated condition of the reservoir 32 and thus an erect condition (not shown) of the penis. To achieve this latter state, the pressurized fluid must enter into the anterior bladder 34 through the port 36 leading to the anterior chamber 34', whereby the bladder 34, bellows 32, and sheath 30 extend longitudinally. This extension effects erection of the penis. Because of the folded configuration of the bellows 32, radial expansion or bulging thereof is limited. Also, the bellows 32 is, preferably, formed of a suitable implant material. It will be appreciated that the entire penile prosthesis 10 of the present invention can be manufactured in suitable sizes and with a variety of biocompatible materials consistent with safe patient usage.

In order for the penis to return to a flaccid condition, the fluid must be expelled from the chamber 34. This occurs, preferably, by remote control operation, and as such the expelled fluid travels through the fluid transfer assembly 20 into the proximal or reservoir chamber assembly 115 in a manner to be more fully described hereinafter.

While the present embodiment describes the utilization of a longitudinally extensible bellows type distal chamber for penile elongation, it envisions that other types of chambers can be used which can become rigid upon pressurized fluid being introduced thereinto to thereby effect an erect penile condition.

Figure 3:
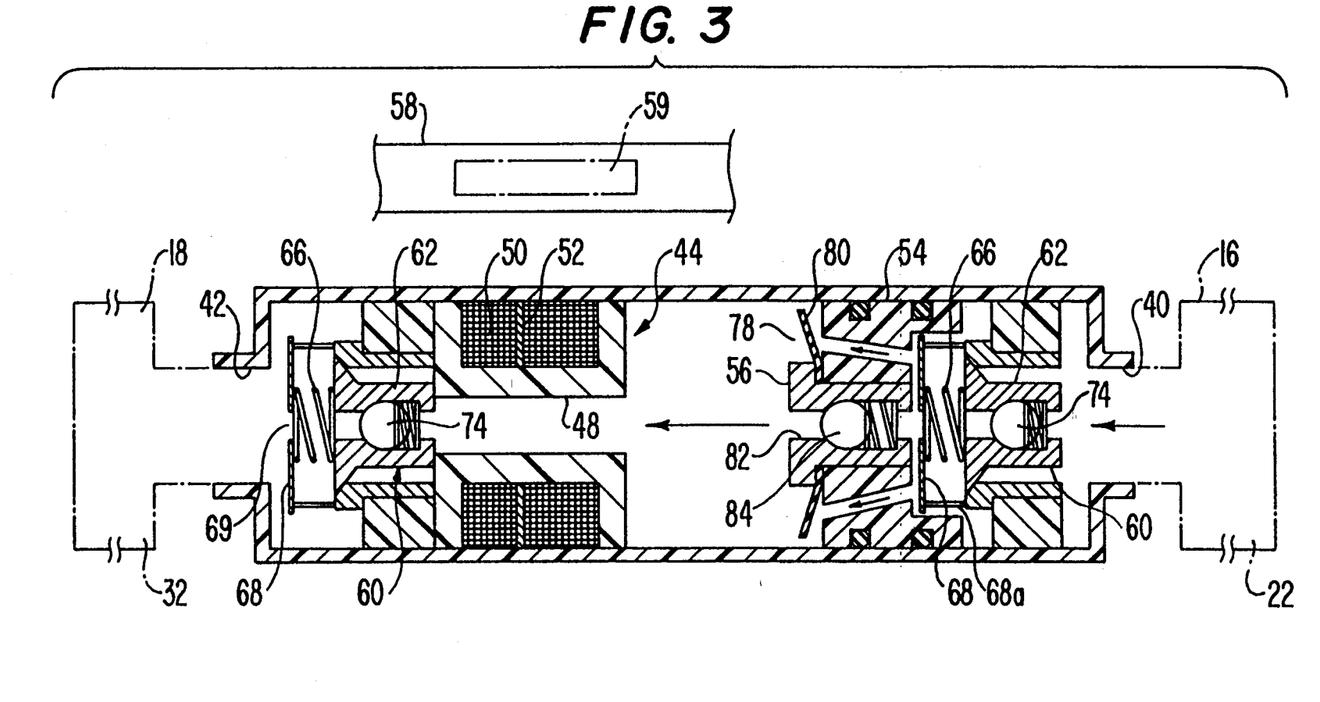
FIG. 3 is an enlarged longitudinal sectional view of a component of the prosthesis in one mode of operation together with a segment of a manual remote control device.
Figure 4:
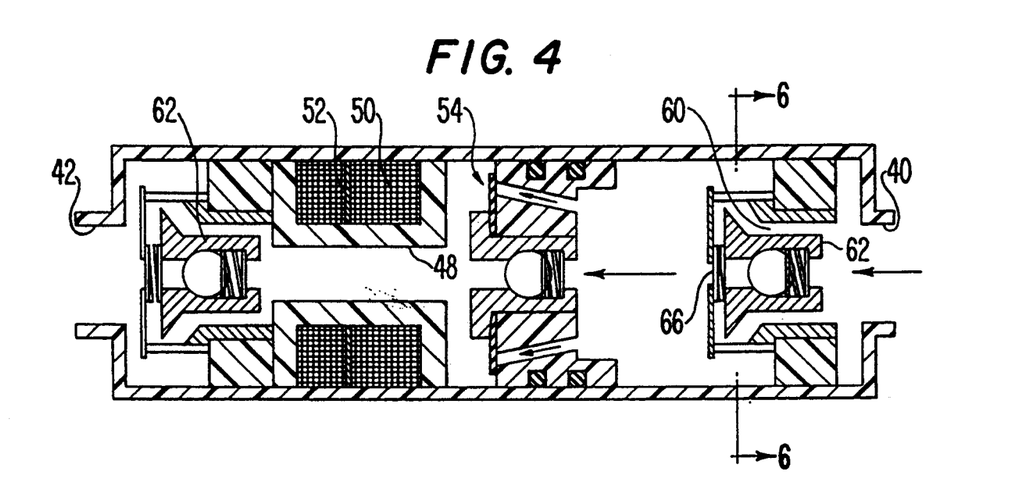
FIGS. 4 and 5 are similar to FIG. 3, but illustrate the components in other conditions of operation.
Figure 5:
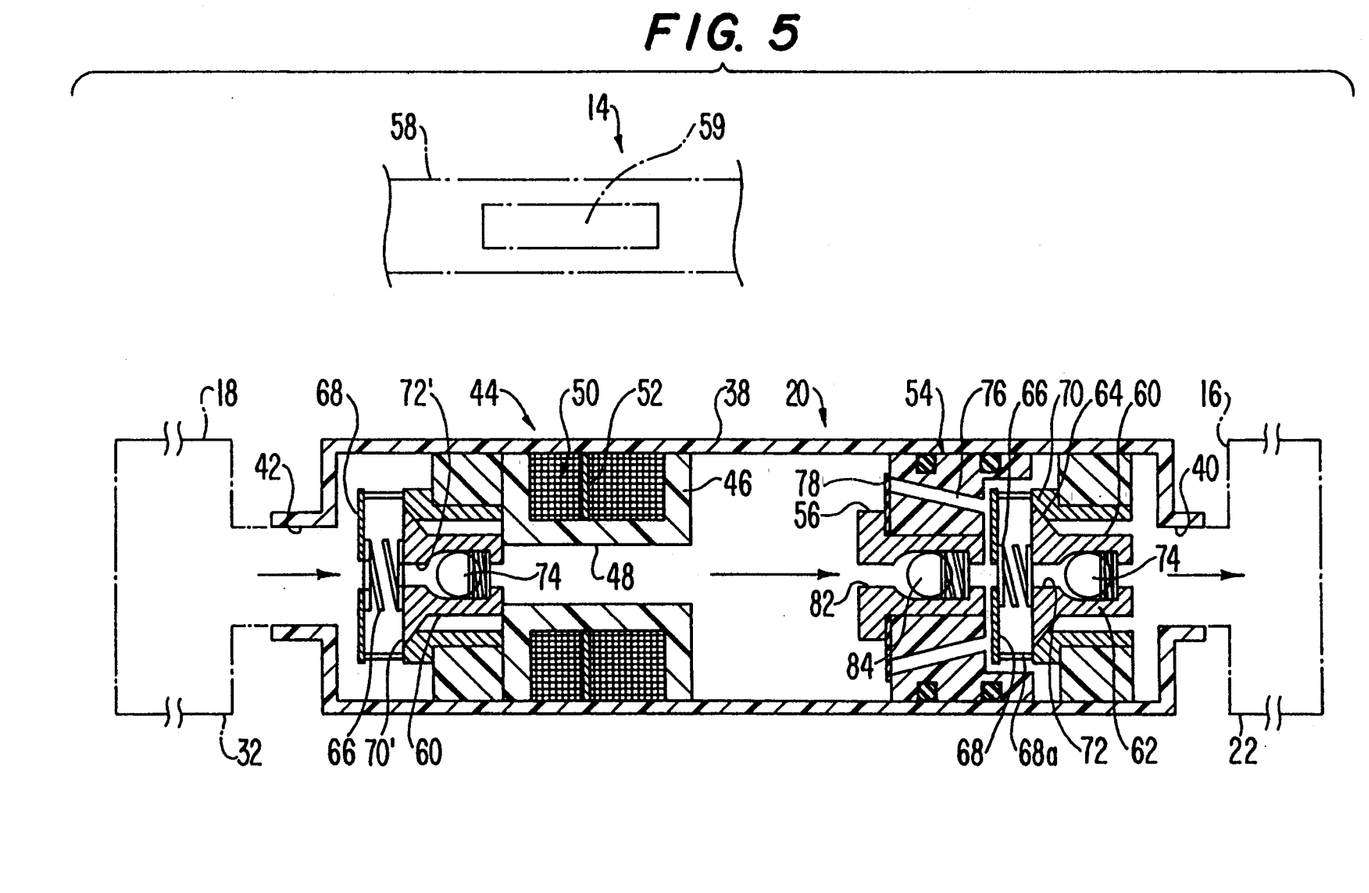
Figure 6:
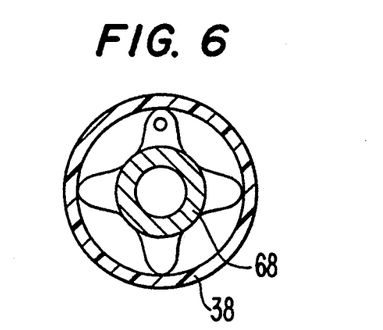
FIG. 6 is a cross-sectional view taken along section line 6—6 in FIG. 3.

Continued reference is made to FIGS. 3-5 for illustrating the fluid transfer assembly 20 for effecting the above fluid transfer operations. The assembly 20 basically includes a cylindrical housing assembly 38. Located at opposite ends thereof are fluid inlet/outlet ports 40, 42. Also, an electromagnetic induction assembly 44 is positioned stationarily intermediate the chamber assemblies 16 and 18. The electromagnetic assembly 44 can be any one of several known types. In this embodiment, it basically includes a stationary bobbin 46 defining a central fluid passage 48 therethrough, a field coil assembly 50 wrapped around the bobbin and having a suitable number of turns sufficient for facilitating the generation of motive forces. The electromagnetic assembly 44 also includes a generally flat annular magnetizable plate 52. A plunger or piston assembly 54 comprises a corresponding magnetizable plug 56 associated with the plate 52 for effecting an electromagnetic circuit with the coil assembly 50 and a plate 52 associated therewith. In this embodiment, electric current is induced in the coil 50, preferably, by a remote handheld electromagnetic device or wand 58. The remote control wand 58 is suitably electrically energized by an appropriate power source (e.g. battery) to selectively create different and opposite polarity electromagnetic fields. The actuating wand 58, as diagrammatically depicted in FIG. 3, includes an electromagnetic assembly 59. The wand 58 is portable and adapted to be held in proximity to the fluid transfer housing 20 for actuating the latter. When the wand assembly 59 is energized it selectively creates either a positive or negative electromagnetic field. Each field induces a current of a given polarity opposing the other. One such field will effect an attractive force between the plate 52 and plug 56 which causes the plunger assembly 54 to move toward the electromagnetic assembly 44. Actuation of the wand 58 to create the opposite polarity causes the assembly 44 to generate a repulsive electromagnetic force that is sufficient in magnitude to displace the plunger assembly 54 in the opposite direction (as viewed in the drawings) for effecting fluid transfer.

The fluid transfer device includes double-acting valve mechanisms 60, 60; each of which cooperates with an appropriate one of the inlet/outlet ports 40, 42; respectively. As illustrated in FIG. 3, the plunger assembly 54 normally contacts the valve mechanism 60 for closing the latter. The plunger assembly 54 normally retains the depicted position (FIG. 3) in the inoperative condition of the prosthesis because of friction between it and the housing 38. In this position the plunger assembly 54 urges the annular frusto-conical valve plug 62 against a valve seat member 64 secured to the housing 38. A biasing spring 66 is interposed between a valve cage 68 which has a central fluid aperture 69 and the cylindrical valve plug 62. The valve plug 62 has a frusto-conical surface 70 which engages the complementary shaped valve seat 64 when the plunger 54 compresses the spring 66. The valve plug 62 includes a central passage 72 having disposed therein a one-.way valve 74. The valve 74 normally retains fluid within the reservoir 22, but allows it to pass into the reservoir 22 when the latter is being filled, such as when the penis is returning to a flaccid condition. The cage 68 includes guide pins 68a which are slidable relative to slots (not shown) in the valve seat member 64. When the valve mechanism 60 is closed, the fluid is retained within the proximal reservoir 22. However, under the influence of a magnetic attractive force, the plunger 54 is moved leftwardly, as viewed in the drawing, towards the electromagnetic assembly 44. This allows the valve plug 62 to move to its open condition because of the pressurized fluid in the reservoir 22 being greater. As a result, fluid can flow from the proximal fluid reservoir 22 into the housing 38, through the passages 76 and one-way flap valve 78 that is defined by a resiliently flexible flap valve disc 80. In this embodiment, the flap valve 80 has its inner annular periphery secured to the central plug 56 which plug and valve define a central passage 82 extending therethrough which cooperates with a one-way valve 84. Fluid leaving the valve 78 then causes a valve mechanism 60, adjacent the inlet/outlet 42, to open by displacing its valve plug 62 to overcome the bias of a spring 68 and move off a valve seat member 64. As a result, the fluid flows into and through inlet/outlet valve 42 to the anterior chamber 34'. The bellows 32 acts to thereby extend along with the sheath and thus effect an erection.

To return the penis to its flaccid condition, the wand 58 is actuated so that it causes the electromagnetic device 44 to generate repulsive electromagnetic forces between it and the plunger 54. Movement of the plunger 54 in the opposite direction (i.e. rightward as viewed in the drawings) creates a relative negative pressure on that side of the valve mechanism 60'. This resulting pressure differential occasioned by such movement is sufficient for purposes of allowing the pressurized fluid in the fluid reservoir 32 to flow through the one-way valve 74 into the housing and through the passage 38. Thereafter, the pressurized fluid opens the one-way valve 84 of the plunger 54 and the one-way valve 74 located adjacent the proximal end of the prosthesis. Accordingly, the fluid flows freely from the distal reservoir 32 to the proximal or storage reservoir 22.

The present invention also envisions that manual compression of the reservoir 32 will generate sufficient pressurize for purposes of moving the fluid and opening the noted one-way valves 74, 84, to thereby allow the fluid in the reservoir 32 to flow into the proximal reservoir 22. It will be understood that manual compression could be used as a safety back-up to effect a flaccid condition in event the electromagnetic system fails. Thus, the prosthesis 12 need only be operated in a remote mode during erection and can rely on manual compression to bring about a return to a flaccid penile condition.

Figure 7:
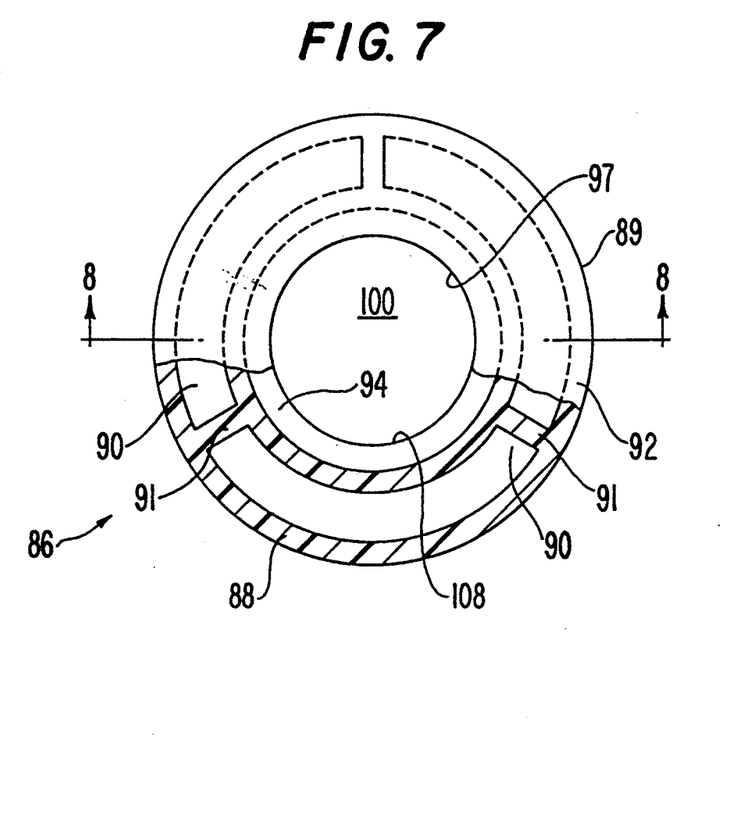
FIG. 7 is a schematic end view of a double-acting valve made according to the invention.
Figure 8:
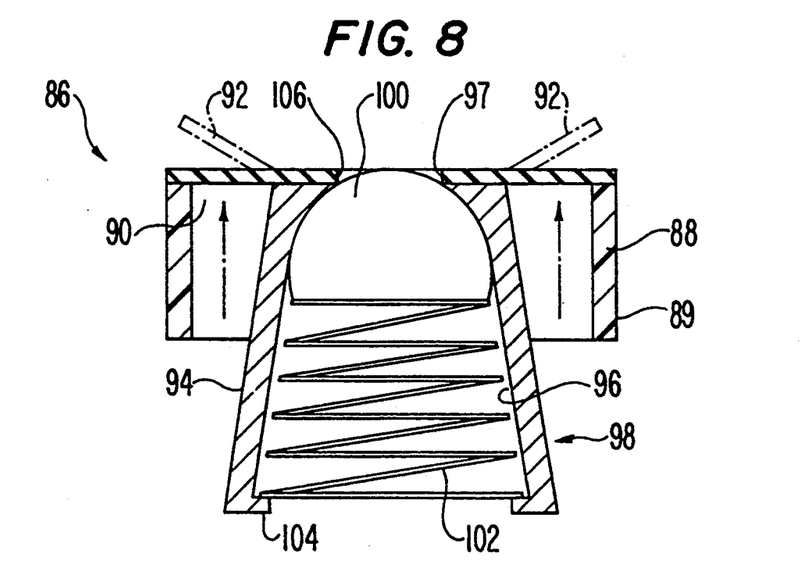
FIG. 8 is a longitudinal section view taken along section line 8—8 in FIG. 7; and, FIG. 9 is a schematic longitudinal section view of a plunger of the present invention.

Reference is now made to FIGS. 7 and 8 for purposes of illustrating an alternate preferred embodiment of a double-acting valve mechanism 86 which is usable in conjunction with the present invention. It will be noted that the valve mechanisms 60 and 60 can be replaced by the construction of double-acting valve mechanisms 86. The valve mechanism 86 is, preferably, plastic and includes a cylindrical member 88 having sidewalls 89 fixedly engaged with the inner walls of the housing. A plurality of arcuate fluid openings 90 are formed in a top wall 91 of the member 88. The openings 90 are normally closed by a flexibly resilient flap valve 92 (see solid line position) having an annular configuration which is made of rubber or the like and which has its inner annular periphery secured to a cone member 94. In the phantom line position of the drawing the flap valve 92 is in the open position. The cone member 94 is hollow and defines a recess 96 for retaining one-way valve 98 that normally blocks an opening 97. The one-way spring biased ball valve 98 itself includes a ball check member 100 having a generally hemispherical shape and a tapered conical spring 102. The spring 102 has its wide end supported by and affixed, as by adhesive bonding, to radially inward directed ridge 104 of the cone 94. The spring 102 serves to normally force the ball check member 100 against a complementary shaped valve seat 106 to close opening 97.

Figure 9:
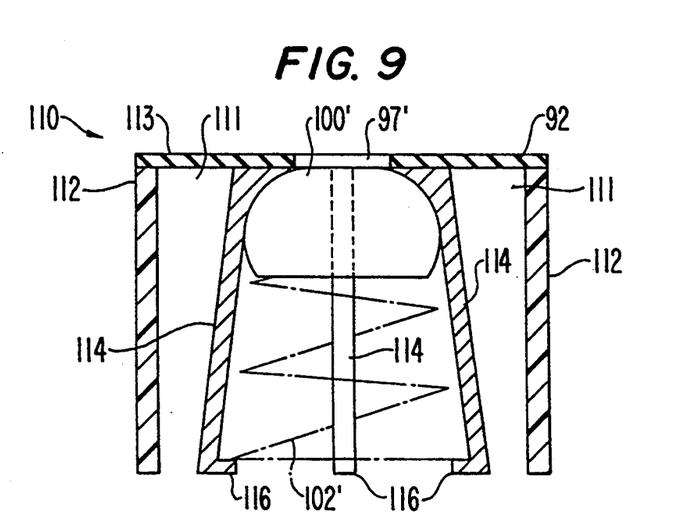

Reference is made to FIG. 9 for illustrating an alternate preferred embodiment of a cylindrical plunger assembly 110 which can be substituted for the plunger assembly 56. The cylindrical plunger assembly 110 is structurally similar to the double-acting valve mechanism 86, but it is intended to slide within the transfer housing as opposed to remaining stationary therein. The plunger assembly 110 includes a generally cylindrical member 112 having a greater height than the corresponding height of cylindrical member 88 of the valve mechanism 86. This facilitates stable sliding movement of the plunger 110 within the housing. A plurality of arcuate openings 111 similar to openings 90 are, preferably, formed in a top wall of the member 112. The openings are normally closed by a flexibly resilient one-way flap valve 113. The flap valve 113 has an annular configuration as the valve 92. Instead of a solid central cone extending from the cylinder member 112 as cone 94 there is provided a plurality of circumferentially spaced apart legs 114 for purposes of reducing plunger weight. The legs 114 house metallic biasing spring 102' and a metallic generally hemispherical shaped ball member 100'. The legs 114 have shoulders 116 upon which the spring is supported and fixedly connected. The spring biased ball member 100' serves to close a central opening 97' formed at the top of the cylinder member 112. In this embodiment, the above noted electromagnetic device 44 will operate upon the metallic nature of the spring and ball member to effect the attraction or repulsion forces necessary to operate the fluid transfer assembly 20.

Figure 10:
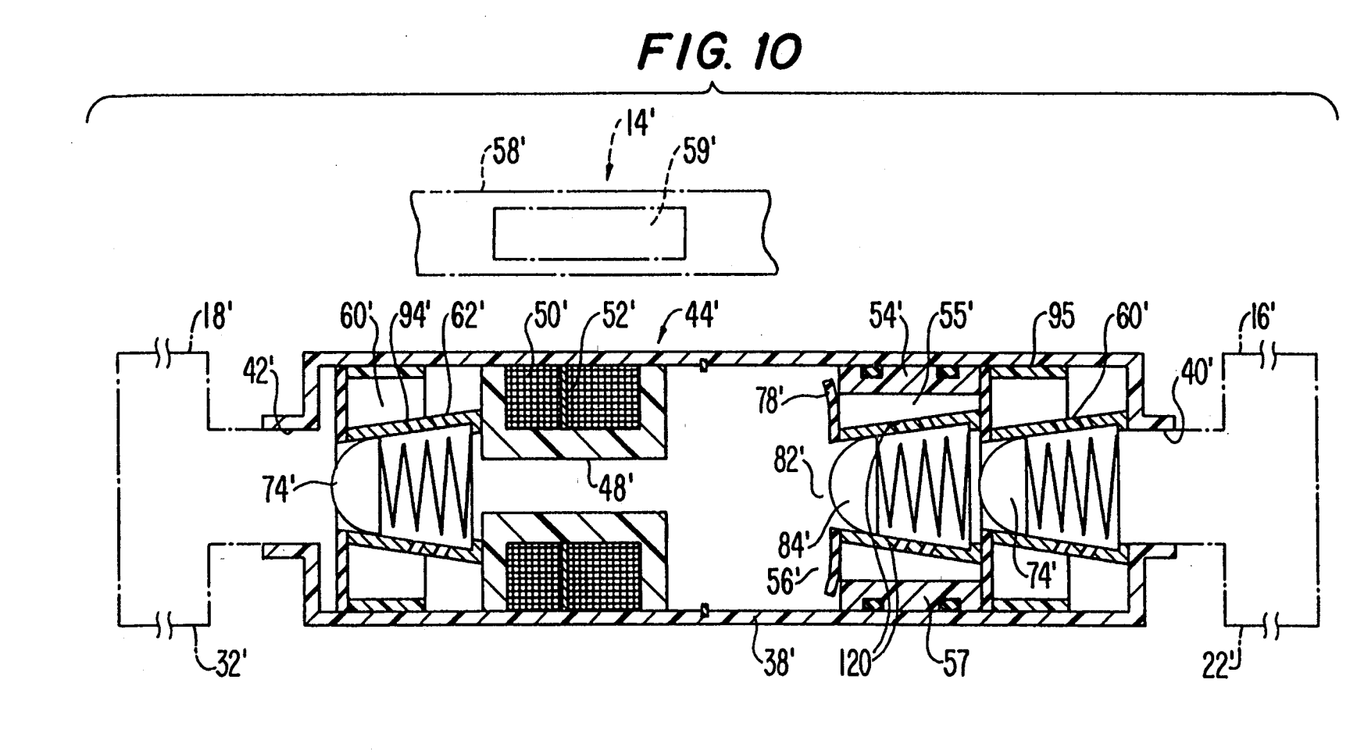
FIG. 10 is a view of another preferred embodiment of the present invention similar to FIG. 3.
Figure 11:
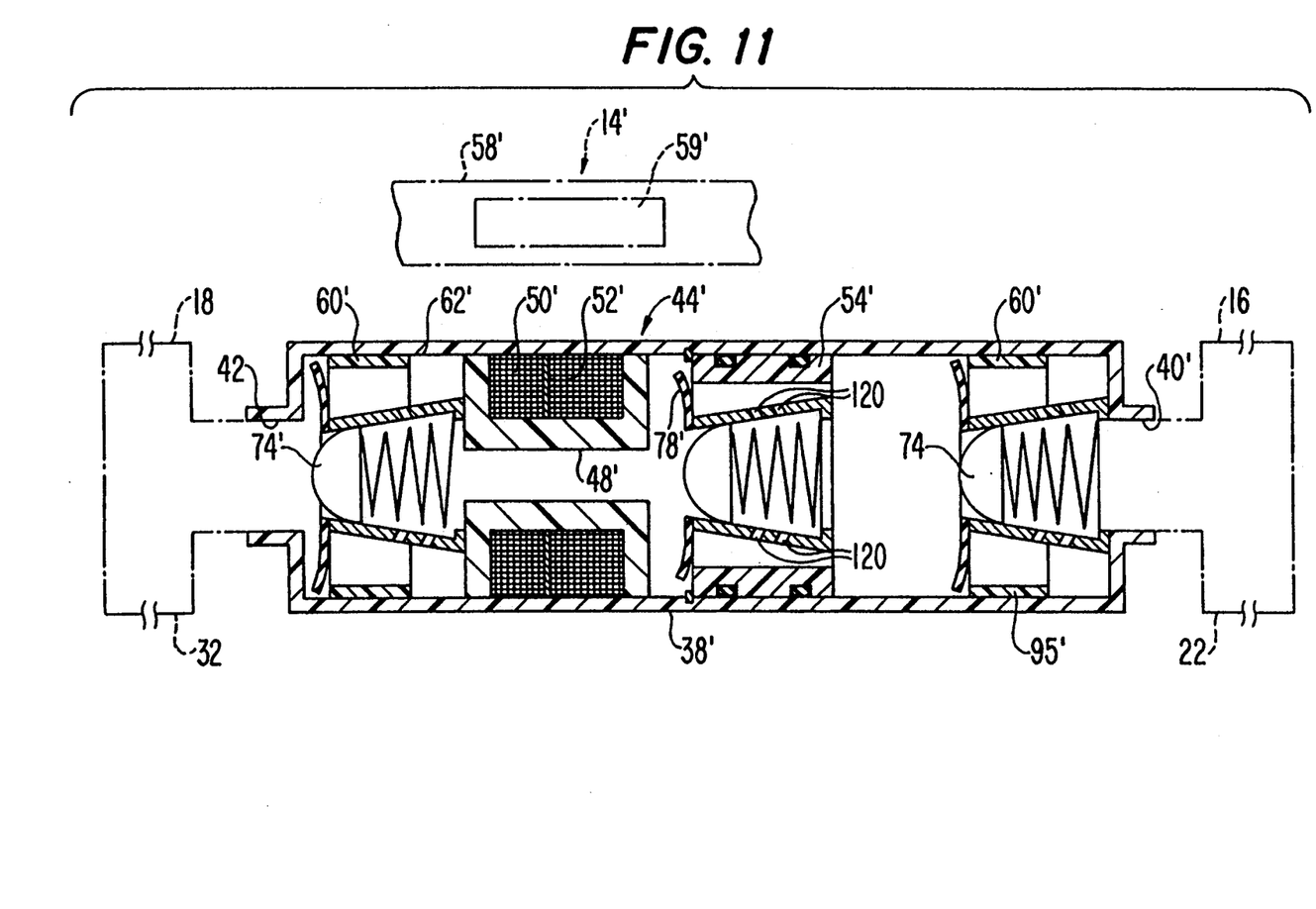
FIGS. 11 and 12 are similar to FIG. 10, but illustrate the components thereof in different conditions of operation.
Figure 12:
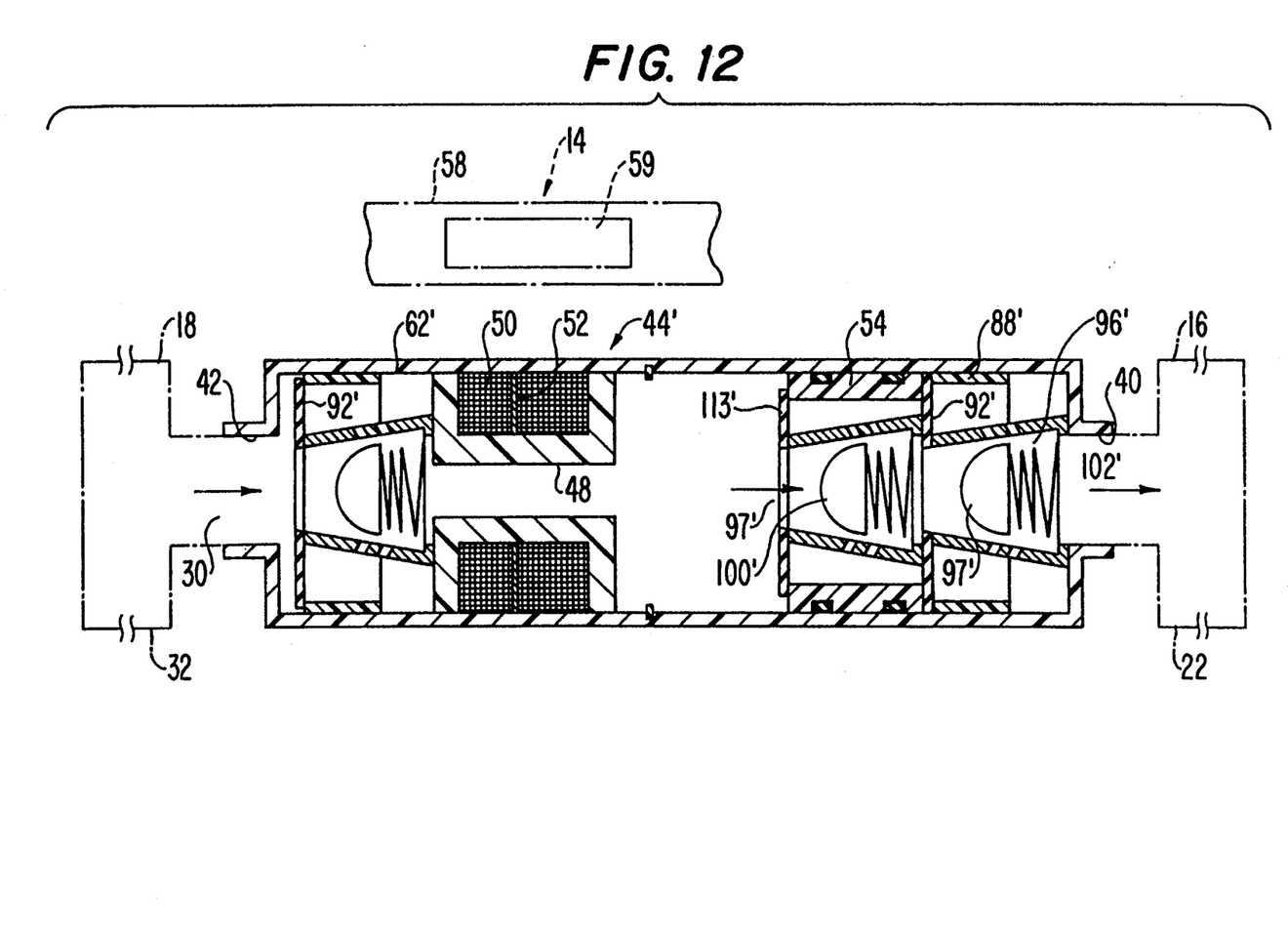

Reference is made to FIGS. 10-12 for illustrating another preferred embodiment of a fluid transfer assembly 20'. Structure of this embodiment which is similar to that of FIGS. 3-5 will be indicated by the same reference numerals with the addition of a prime marking. This embodiment includes a cylindrical housing assembly 38' having at opposite ends thereof inlet/outlet ports 40', 42'. Also, the fluid transfer assembly 20' includes on electromagnetic inductor assembly 44' which is positioned stationarily intermediate the chamber assemblies 16', 18'. The electromagnetic assembly 44' can be any one of several known types. Structural and functional details of the operation of the electromagnetic assembly 44' are like that described in the first embodiment and need not be mentioned. A plunger or piston assembly 54' includes a central body 56' having a plurality of central and spaced ribs 55 connecting the former to a cylindrical member 57 having its external periphery in slidable and sealing engagement within the internal wall of the housing 38'. The central body 56' defines a conical recess and passage 82' for a biased one-way spring valve member 84'. The metallic spring and ball valve effect an electromagnetic circuit with a coil 50' and its associated plate 52' for displacing the plunger assembly 54' in opposite directions. Also, in this embodiment, the electric current is induced in the coil 50', preferably, by the handheld electromagnetic wand 58'. The wand 58' is suitably electrically energized by an appropriate power source (e.g. battery) to selectively create opposite polarity electromagnetic fields having different magnitudes The actuating wand 58', includes an electromagnetic assembly 59' and thus a detailed description is not necessary for understanding this embodiment since the wand 58' and assembly 59' are like that described above in a previous embodiment.

In this preferred embodiment, a pair of opposed double-acting valve mechanisms 60', 60' each of which cooperates with a corresponding one of the inlet/outlet ports 40', 42'. These valve mechanisms 60', 60' are similar to those described above in connection with FIG. 8. As illustrated in FIG. 10, the plunger assembly 54' contacts the valve mechanism 60', so as to close the flap valve of the latter. The plunger 54' normally retains the depicted position (FIG. 10) when the prosthesis is in the inoperative condition because of the friction between it and the inside walls of the housing 38'. In this position, the plunger assembly 54' tends to force an annular flexibly resilient rubber flap valve 92' against a valve seat defined by a cone member 94' so as to cover fluid openings 90'. Also, in this embodiment, the cone member 94' is preferably, made of steel. The valve mechanisms 60' have peripheral sides 95' and each hollow cone member 94' is centrally attached to the cylinder 88' and defines a conical recess 96' and opening 97' for allowing passage of fluid therethrough in a manner described above. Each cone member 94' has a plurality of openings 120 which are adapted not to impede the free flow of the pressurized fluid between the valve mechanisms 60', 60' and plunger assembly 54'. Also, the cylinder 57 of the plunger 54' is longer than the cylinder 88' of the valve mechanism 60'. This results in the radial space between the base of the cone and the inside cylinder wall 57 being shorter in the plunger 56' than is the comparable space in the valve mechanism 60'. The number and size of the openings 120 compensate for the narrower radial passage between the outer cylinder wall 57 and the central cone shaped body 56'. The operation of this embodiment of the fluid transfer assembly 20' is self-evident given the above description of its structure and the operations of the previous embodiments.

Changes may be made in the construction and operation of various elements, parts, and assemblies described herein and changes may be made in the steps or the sequence of steps of operating the system described herein without departing from the spirit and scope of the invention as defined by the following claims.

What is claimed is:

1. A remote controllable penile prosthetic system, comprising:
an implantable penile prosthesis including, first fluid chamber means located adjacent a distal end of said prosthesis, and being inflatable with pressurizing fluid, second fluid chamber means for selectively storing fluid and located adjacent a proximal end of said prosthesis opposite said first fluid chamber means, fluid transfer means coupled to and cooperating with said first and second chamber means and selectively transferring fluid between said first and second chamber means in response to remote control operation thereof, so as to cause an erect condition of the penis in one mode and to permit withdrawal of the fluid therefrom to effect a flaccid condition of the penis in a second mode, said transfer means including, a displaceable plunger, energizable electromagnetic means for selectively displacing said plunger within said fluid transfer means in response to energization of said electromagnetic means, valve means associated with said fluid transfer means for allowing fluid flow between said first and second chamber means; and, energizing means for energizing said energizable means from a remote location.

2. The system of claim 1 wherein said fluid transfer means includes a housing coupled to and between said first and second chamber means and defining an elongated housing chamber for fluidly coupling said first and second chamber means; said energizable means being positioned within said housing chamber and said plunger being movable within said housing chamber in at least one direction in response to selective energization of said energizable means for allowing fluid to flow from said second chamber means through said valve means to said first chamber means.

3. The system of claim 2 wherein said valve means includes a pair of double-acting valves, each of said double-acting valves being located adjacent an end of said housing and being coupled to respective ones of said first and second chamber means, and said plunger including a double-acting valve for allowing fluid flow therethrough in opposite directions.

4. The system of claim 2 wherein said first fluid chamber means is compressible manually to allow fluid to be forced therefrom.

5. The system of claim 1 wherein said energizing means includes a portable wand containing an electromagnetic field generator which generates selective ones of electromagnetic fields of opposite polarity so as to induce currents of opposite polarity in said energizable means.

6. The system of claim 3 wherein each of said double-acting valves includes at least one passage having a one-way flap valve therein, said passage being opened and closed by said flap valve, and a second passage having a ball type check valve therein, said second passage being opened and closed by said ball type check valve.

7. The system of claim 4 wherein said first fluid chamber means is elongatable.

8. The system of claim 7 wherein said first fluid chamber means includes a bladder that receives pressurizing fluid therein for elongated expansion.

9. The system of claim 2 wherein said energizable means includes a fluid passage therethrough for allowing passage of fluid between said first and second fluid chamber means.

10. The system of claim 2 wherein said second fluid chamber means includes a bladder and a cage assembly connected to said housing for allowing unimpeded expansion and contraction when said prosthesis is implanted and said cage adapted to facilitate securement of said prosthesis to a base of a penis.

11. The system of claim 2 wherein said plunger includes at least one passage having a one-way flap valve therein, said passage being opened and closed by said flap valve, and a second passage defined by a central member, said second passage being opened and closed by a one-way valve, said central member having fluid passage openings therein which are arranged to enhance flow of fluid through said central member between said one and second passage.

12. A unitary penile prosthetic apparatus which is remote controllable, said apparatus comprising:

a fully implantable, self contained, penile prosthesis including, first fluid chamber means located adjacent a distal end of said prosthesis, and being alternately inflatable with pressurizing fluid so as to cause an erect condition of the penis, or deflatable by withdrawal of the fluid therefrom to effect a flaccid condition in the penis, second fluid chamber means located adjacent a proximal end of said prosthesis and for selectively storing fluid, fluid transfer means coupled to and cooperating with said first and second chamber means for selectively transferring fluid between said first and second chamber means in response to remote control operation thereof; and, said transfer means including a displaceable plunger, stationary energizable electromagnetic means for displacing said plunger within said fluid transfer means in response to actuation of said electromagnetic means, and valve means for allowing fluid flow between said first and second chamber means.

13. The apparatus of claim 12 wherein said fluid transfer means includes a housing coupled to and between said first and second chamber means and defining an elongated housing chambers said energizable electromagnetic means being positioned within said housing chamber and said plunger being movable within said housing chamber in at least one direction in response to selective energization of said energizable means for allowing fluid to flow from said second chamber means through said valve to said first chamber means.

14. The apparatus of claim 13 wherein said valve means includes a pair of double acting valves, each located in said housing chamber adjacent, respectively, to said first and second chamber means, and said plunger includes a double acting valve for allowing fluid flow therethrough in opposite directions.

15. The apparatus of claim 14 wherein said first fluid chamber means is compressible manually to allow fluid to be forced therefrom.

16. The apparatus of claim 12 further comprising energizing means including a portable wand containing an electromagnetic field generator which generates selective ones of electromagnetic fields of opposite polarity so as to induce currents of opposite polarity in said energizable electromagnetic means.

17. The apparatus of claim 14 wherein said double-acting valve in said plunger includes a passage having one-way flap valve therein and a passage having a ball type check valve therein.

18. The apparatus of claim 15 wherein said first fluid chamber means is elongatable.

19. The apparatus of claim 18 wherein said first fluid chamber means includes a bladder that receives pressurizing fluid therein for elongated expansion.

20. The apparatus of claim 13 wherein said energizable electromagnetic means includes a fluid passage therethrough for allowing passage of fluid between said first and second fluid chamber means.

21. The apparatus of claim 13 wherein said second fluid chamber means includes a bladder and a cage assembly connected to said housing for allowing unsuspected expansion and contraction when said prosthesis is implanted and said cage adapted to facilitate securement of said prosthesis to a base of a penis.

22. The apparatus of claim 13 wherein said plunger includes at least one passage having a one-way flap valve therein, said passage being opened and closed by said flap valve, and a second passage defined by a central member, said second passage having a one-way valve therein, said central member having fluid passage openings therein which are arranged to enhance flow of fluid through said central member between said one and second passages.

* * * * *